(12) United States Patent
Childers et al.

(10) Patent No.: US 8,206,339 B2
(45) Date of Patent: *Jun. 26, 2012

(54) SYSTEM FOR MONITORING AND CONTROLLING PERITONEAL DIALYSIS

(75) Inventors: Robert W. Childers, New Port Richey, FL (US); Vital Eerlingen, Leuven (BE); Patrick Balteau, Bothey (BE); Duane Belongie, Minneapolis, MN (US)

(73) Assignee: Baxter International Inc., Deerfield, IL (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/408,432

(22) Filed: Mar. 20, 2009

(65) Prior Publication Data

US 2009/0198174 A1 Aug. 6, 2009

Related U.S. Application Data

(60) Continuation of application No. 10/446,068, filed on May 27, 2003, now Pat. No. 7,507,220, which is a division of application No. 10/078,568, filed on Feb. 14, 2002, now Pat. No. 6,592,542, which is a continuation of application No. 09/501,778, filed on Feb. 10, 2000, now Pat. No. 6,497,676.

(51) Int. Cl.
  *A61M 1/00* (2006.01)
(52) U.S. Cl. .......................................... 604/29; 604/5.01
(58) Field of Classification Search ................... 604/19, 604/27, 28, 29, 4.01, 5.01–5.04
  See application file for complete search history.

(56) References Cited

U.S. PATENT DOCUMENTS

| | | | |
|---|---|---|---|
| 2,286,613 | A | 1/1942 | Fuller |
| 3,327,115 | A | 6/1967 | Barlett |
| 3,485,245 | A | 12/1969 | Lahr et al. |
| 3,620,215 | A | 11/1971 | Tysk et al. |

(Continued)

FOREIGN PATENT DOCUMENTS

DE 1964735 7/1971

(Continued)

OTHER PUBLICATIONS

Defendants' Preliminary Invalidity Contentions for U.S. Patent No. 5,421,823, *Baxter Healthcare Corporation v. Fresenius Medical Care Holdings*, Case No. C 07-01359 PJH (JL), filed Aug. 24, 2007.

(Continued)

*Primary Examiner* — Matthew F Desanto
(74) *Attorney, Agent, or Firm* — K&L Gates LLP

(57) ABSTRACT

A peritoneal dialysis system includes a cycler operable with a disposable cassette, the cassette connected to a patient line, the cassette capable of fluid communication with a catheter having access to a patient's peritoneal cavity, the cycler configured to: (i) convey dialysis fluid to the peritoneal cavity through the patient line and the catheter during a patient fill phase; (ii) allow the dialysis fluid to dwell within the peritoneal cavity during a patient dwell phase; (iii) convey dialysis fluid away from the peritoneal cavity through the patient line and the catheter during a patient drain phase; and (iv) sense, at first and second sensing locations of the disposable cassette via first and second pressure sensors, an intraperitoneal pressure through the catheter to optimize an amount of fluid conveyed during the patient fill phase, so that the peritoneal cavity is not overpressurized during the patient dwell phase.

24 Claims, 8 Drawing Sheets

U.S. PATENT DOCUMENTS

| | | | |
|---|---|---|---|
| 3,626,670 A | 12/1971 | Pecker | |
| 3,656,873 A | 4/1972 | Schiff | |
| 3,689,204 A | 9/1972 | Prisk | |
| 3,703,959 A | 11/1972 | Raymond | |
| 3,707,967 A | 1/1973 | Kitrilakis et al. | |
| 3,709,222 A | 1/1973 | DeVries | |
| 3,792,643 A | 2/1974 | Scheafer | |
| 3,902,490 A | 9/1975 | Jacobsen | |
| 3,955,901 A | 5/1976 | Hamilton | |
| 3,976,574 A | 8/1976 | White | |
| 3,979,284 A | 9/1976 | Granger | |
| 4,086,653 A | 4/1978 | Gernes | |
| 4,126,132 A | 11/1978 | Portner et al. | |
| 4,140,118 A | 2/1979 | Jassawalla | |
| 4,142,524 A | 3/1979 | Jassawalla et al. | |
| 4,158,530 A | 6/1979 | Bernstein | |
| 4,181,245 A | 1/1980 | Garrett et al. | |
| 4,187,057 A | 2/1980 | Xanthopoulos | |
| 4,199,307 A | 4/1980 | Jassawalla | |
| 4,235,231 A | 11/1980 | Schindler et al. | |
| 4,236,880 A | 12/1980 | Archibald | |
| 4,252,651 A | 2/1981 | Soderstrom | |
| 4,265,601 A | 5/1981 | Mandroian | |
| 4,273,121 A | 6/1981 | Jassawalla | |
| 4,277,226 A | 7/1981 | Archibald | |
| 4,303,376 A | 12/1981 | Seikmann | |
| 4,310,141 A | 1/1982 | Tamura | |
| 4,316,466 A | 2/1982 | Babb | |
| 4,375,346 A | 3/1983 | Kraus et al. | |
| 4,381,003 A | 4/1983 | Buoncristiani | |
| 4,381,005 A | 4/1983 | Bujan | |
| 4,382,753 A | 5/1983 | Archibald | |
| 4,391,600 A | 7/1983 | Archibald | |
| 4,410,322 A | 10/1983 | Archibald | |
| 4,430,048 A | 2/1984 | Fritsch | |
| 4,456,218 A | 6/1984 | Kawabata et al. | |
| 4,468,222 A | 8/1984 | Lundquist | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,504,038 A | 3/1985 | King | |
| 4,530,759 A | 7/1985 | Schal | |
| 4,552,552 A | 11/1985 | Polaschegg et al. | |
| 4,559,036 A | 12/1985 | Wunsch | |
| 4,559,044 A | 12/1985 | Robinson et al. | |
| 4,560,472 A | 12/1985 | Granzow et al. | |
| 4,585,436 A | 4/1986 | Davis et al. | |
| 4,613,327 A | 9/1986 | Tegrarian et al. | |
| 4,618,343 A | 10/1986 | Polaschegg | |
| RE32,303 E | 12/1986 | Lasker et al. | |
| 4,634,430 A | 1/1987 | Polaschegg | |
| 4,639,245 A | 1/1987 | Pastrone et al. | |
| 4,642,098 A | 2/1987 | Lundquist | |
| 4,648,810 A | 3/1987 | Schippers et al. | |
| 4,648,872 A | 3/1987 | Kamen | |
| 4,657,490 A | 4/1987 | Abbott | |
| 4,694,848 A | 9/1987 | Jorgensen et al. | |
| 4,703,773 A | 11/1987 | Hansen et al. | |
| 4,717,117 A | 1/1988 | Cook | |
| 4,718,890 A | 1/1988 | Peabody | |
| 4,747,822 A | 5/1988 | Peabody | |
| 4,769,134 A * | 9/1988 | Allan et al. | 210/87 |
| 4,778,356 A | 10/1988 | Hicks | |
| 4,778,451 A | 10/1988 | Kamen | |
| 4,784,576 A | 11/1988 | Bloom et al. | |
| 4,808,161 A | 2/1989 | Kamen | |
| 4,816,019 A | 3/1989 | Kamen | |
| 4,818,186 A | 4/1989 | Pastrone et al. | |
| 4,818,190 A | 4/1989 | Pelmulder et al. | |
| 4,823,552 A | 4/1989 | Ezell et al. | |
| 4,826,482 A | 5/1989 | Kamen | |
| 4,828,545 A | 5/1989 | Epstein et al. | |
| 4,830,586 A | 5/1989 | Herter et al. | |
| 4,842,582 A | 6/1989 | Mahurkar | |
| 4,842,584 A | 6/1989 | Pastrone | |
| 4,848,722 A | 7/1989 | Webster | |
| 4,850,805 A | 7/1989 | Madsen et al. | |
| 4,852,851 A | 8/1989 | Webster | |
| 4,855,356 A | 8/1989 | Holub et al. | |
| 4,859,319 A | 8/1989 | Borsari | |
| 4,865,584 A | 9/1989 | Epstein et al. | |
| 4,872,813 A | 10/1989 | Gorton et al. | |
| 4,886,432 A | 12/1989 | Kimberlin | |
| 4,927,411 A | 5/1990 | Pastrone et al. | |
| 4,942,735 A | 7/1990 | Mushika et al. | |
| 5,002,471 A | 3/1991 | Perlov | |
| 5,006,050 A | 4/1991 | Cooke et al. | |
| 5,062,774 A | 11/1991 | Kramer et al. | |
| 5,088,515 A | 2/1992 | Kamen | |
| 5,094,820 A | 3/1992 | Maxwell et al. | |
| 5,098,262 A | 3/1992 | Wrecker et al. | |
| 5,108,844 A | 4/1992 | Blumberg et al. | |
| 5,125,891 A | 6/1992 | Hossain et al. | |
| 5,141,493 A | 8/1992 | Jacobsen et al. | |
| 5,163,900 A | 11/1992 | Wortrich | |
| 5,176,956 A | 1/1993 | Jevne et al. | |
| 5,178,182 A | 1/1993 | Kamen | |
| 5,185,084 A | 2/1993 | Lapidus et al. | |
| 5,195,960 A | 3/1993 | Hossain et al. | |
| 5,207,642 A | 5/1993 | Orkin et al. | |
| 5,241,985 A | 9/1993 | Faust et al. | |
| 5,245,693 A | 9/1993 | Ford et al. | |
| 5,247,434 A | 9/1993 | Peterson et al. | |
| 5,252,044 A | 10/1993 | Raines et al. | |
| 5,292,306 A | 3/1994 | Wynkoop et al. | |
| 5,302,093 A | 4/1994 | Owens et al. | |
| 5,316,452 A | 5/1994 | Bogen et al. | |
| 5,332,372 A | 7/1994 | Reynolds | |
| 5,344,292 A | 9/1994 | Rabenau et al. | |
| 5,350,357 A | 9/1994 | Kamen et al. | |
| 5,378,126 A | 1/1995 | Abrahamson et al. | |
| 5,389,243 A | 2/1995 | Kaplan | |
| 5,397,222 A | 3/1995 | Moss et al. | |
| 5,409,355 A | 4/1995 | Brooke | |
| 5,415,528 A | 5/1995 | Ogden et al. | |
| 5,421,208 A | 6/1995 | Packard et al. | |
| 5,421,823 A | 6/1995 | Kamen et al. | |
| 5,429,485 A | 7/1995 | Dodge | |
| 5,431,626 A | 7/1995 | Bryant et al. | |
| 5,458,468 A | 10/1995 | Ye et al. | |
| 5,474,683 A | 12/1995 | Bryant et al. | |
| 5,476,368 A | 12/1995 | Rabenau et al. | |
| 5,482,440 A | 1/1996 | Dennehey et al. | |
| 5,487,649 A | 1/1996 | Dorsey, III et al. | |
| 5,522,769 A | 6/1996 | DeGuiseppi | |
| 5,526,844 A | 6/1996 | Kamen | |
| 5,533,389 A | 7/1996 | Kamen et al. | |
| 5,536,412 A | 7/1996 | Ash | |
| 5,542,919 A | 8/1996 | Simon et al. | |
| 5,554,013 A | 9/1996 | Owens et al. | |
| 5,556,263 A | 9/1996 | Jacobsen et al. | |
| 5,570,716 A | 11/1996 | Kamen et al. | |
| 5,575,310 A | 11/1996 | Kamen et al. | |
| 5,578,012 A | 11/1996 | Kamen et al. | |
| 5,580,460 A | 12/1996 | Polaschegg | |
| 5,586,868 A | 12/1996 | Lawless et al. | |
| 5,588,816 A | 12/1996 | Abbott et al. | |
| 5,591,344 A | 1/1997 | Kenley et al. | |
| 5,603,354 A | 2/1997 | Jacobsen et al. | |
| 5,609,572 A | 3/1997 | Lang | |
| 5,620,312 A | 4/1997 | Hyman et al. | |
| 5,628,908 A | 5/1997 | Kamen et al. | |
| 5,630,935 A | 5/1997 | Treu | |
| 5,632,606 A | 5/1997 | Jacobsen et al. | |
| 5,634,896 A | 6/1997 | Bryant et al. | |
| 5,645,734 A | 7/1997 | Kenley et al. | |
| 5,669,764 A | 9/1997 | Behringer et al. | |
| 5,718,692 A | 2/1998 | Schon et al. | |
| 5,722,947 A | 3/1998 | Jeppsson et al. | |
| 5,758,563 A | 6/1998 | Robinson | |
| 5,788,671 A | 8/1998 | Johnson | |
| 5,790,752 A | 8/1998 | Anglin et al. | |
| 5,807,075 A | 9/1998 | Jacobsen et al. | |
| 5,814,004 A | 9/1998 | Tamari | |
| 5,816,779 A | 10/1998 | Lawless et al. | |
| 5,836,908 A | 11/1998 | Beden et al. | |
| 5,871,566 A | 2/1999 | Rutz | |

| | | | |
|---|---|---|---|
| 5,919,369 | A | 7/1999 | Ash |
| 5,921,951 | A | 7/1999 | Morris |
| 5,924,975 | A | 7/1999 | Goldowsky |
| 5,931,647 | A | 8/1999 | Jacobsen et al. |
| 5,938,634 | A * | 8/1999 | Packard ........................ 604/29 |
| 5,944,495 | A | 8/1999 | Jacobsen et al. |
| 5,944,684 | A | 8/1999 | Roberts et al. |
| 5,965,433 | A | 10/1999 | Gardetto et al. |
| 5,989,423 | A | 11/1999 | Kamen et al. |
| 6,007,310 | A | 12/1999 | Jacobsen et al. |
| 6,017,194 | A | 1/2000 | North, Jr. |
| 6,030,359 | A | 2/2000 | Nowosielski |
| 6,036,668 | A | 3/2000 | Mathis |
| 6,041,801 | A | 3/2000 | Gray et al. |
| 6,065,941 | A | 5/2000 | Gray et al. |
| 6,126,403 | A | 10/2000 | Yamada |
| 6,129,699 | A | 10/2000 | Haight et al. |
| 6,165,154 | A | 12/2000 | Gray et al. |
| 6,208,107 | B1 | 3/2001 | Maske et al. |
| 6,210,361 | B1 | 4/2001 | Kamen et al. |
| 6,223,130 | B1 | 4/2001 | Gray et al. |
| 6,228,047 | B1 | 5/2001 | Dadson |
| 6,231,320 | B1 | 5/2001 | Lawless et al. |
| 6,234,991 | B1 | 5/2001 | Gorsuch |
| 6,234,997 | B1 | 5/2001 | Kamen et al. |
| 6,245,039 | B1 | 6/2001 | Brugger et al. |
| 6,248,093 | B1 | 6/2001 | Moberg |
| 6,254,567 | B1 * | 7/2001 | Treu et al. ........................ 604/29 |
| 6,270,673 | B1 | 8/2001 | Belt et al. |
| 6,280,408 | B1 | 8/2001 | Sipin |
| 6,302,653 | B1 | 10/2001 | Bryant et al. |
| 6,364,857 | B1 | 4/2002 | Gray et al. |
| 6,382,923 | B1 | 5/2002 | Gray |
| 6,416,293 | B1 | 7/2002 | Bouchard et al. |
| 6,491,656 | B1 * | 12/2002 | Morris ........................ 604/6.09 |
| 6,491,658 | B1 | 12/2002 | Miura et al. |
| 6,497,676 | B1 * | 12/2002 | Childers et al. ................. 604/29 |
| 6,595,948 | B2 | 7/2003 | Suzuki et al. |
| 6,743,201 | B1 | 6/2004 | Dönig |
| 6,814,547 | B2 | 11/2004 | Childers et al. |
| 6,949,079 | B1 | 9/2005 | Westberg et al. |
| 7,004,924 | B1 | 2/2006 | Brugger et al. |
| 7,033,539 | B2 | 4/2006 | Krensky et al. |
| 2001/0018937 | A1 | 9/2001 | Nemoto |
| 2002/0045851 | A1 | 4/2002 | Suzuki et al. |
| 2005/0118038 | A1 | 6/2005 | Gray et al. |

FOREIGN PATENT DOCUMENTS

| | | |
|---|---|---|
| EP | 0028371 | 5/1981 |
| EP | 0 033 096 | 8/1981 |
| EP | 0 052 004 | 5/1982 |
| EP | 0 097 432 | 1/1984 |
| EP | 0 157 024 | 10/1985 |
| EP | 0 206 195 | 12/1986 |
| EP | 0204260 | 12/1986 |
| EP | 0319272 | 6/1989 |
| EP | 0402505 | 12/1990 |
| EP | 0011935 | 5/1991 |
| EP | 0248632 | 4/1992 |
| EP | 0 660 725 | 7/1995 |
| FR | 2371931 | 6/1978 |
| FR | 2440740 | 6/1980 |
| GB | 1326236 | 8/1973 |
| SE | 331736 | 1/1971 |
| WO | WO 84/02473 | 7/1984 |
| WO | WO 85/04813 | 11/1985 |
| WO | WO 86/01115 | 2/1986 |
| WO | 87/05223 | 9/1987 |
| WO | 89/01795 | 3/1989 |
| WO | 90/13795 | 11/1990 |
| WO | WO 91/02484 | 3/1991 |
| WO | WO 92/15349 | 9/1992 |
| WO | WO 93/01845 | 2/1993 |
| WO | 94/20158 | 9/1994 |
| WO | WO 95/35124 | 12/1995 |
| WO | WO 99/06082 | 2/1999 |
| WO | WO 01/91829 | 12/2001 |

OTHER PUBLICATIONS

Defendants' Supplemental Invalidity Contentions for U.S. Patent No. 5,421,823, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 6,503,062, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 6,808,369, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 5,324,422, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 5,438,510, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 6,814,547, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 5,431,626, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 6,929,751, *Baxter Healthcare Corporation* v. *Fresenius Medical Care Holdings*, Case No. C 07-01359 PJH (JL), filed Jan. 31, 2008.

Defendants' Preliminary Invalidity Contentions for U.S. Patent No. 7,083,719, *Baxter Healthcare Corporation* v. *Fresenius Medical Care Holdings*, Case No. C 07-01359 PJH (JL), filed Jan. 31, 2008.

Defendants' Final Invalidity Contentions for U.S. Patent No. 6,814,547, *Baxter Healthcare Corporation* v. *Fresenius Medical Care Holdings*, Case No. C 07-01359 PJH (JL), filed Apr. 1, 2009.

Fresenius 90/2 Peritoneal Therapy Cycler (on information and belief, on sale in United States by 1991).

Blumenkrantz et al., Applications of the Redy Sorbent System to Hemodialysis and Peritoneal Dialysis, Artificial Organs, vol. 3, No. 3 (Aug. 1979).

Blumenkrantz et al., Development of a Sorbent Peritoneal Dialysate Regeneration System—A Progress Report, European Dialysis and Transplant Association 1978.

Blumenkrantz and Roberts, Progress in Peritoneal Dialysis: a Historical Prospective, Contributions to Nephrology, vol. 17, pp. 101-10 (1979).

Diaz-Buxo, CCPD is even better than CAPD, Kidney International, vol. 28, Suppl. 17, pp. S-26-S-28 (1985).

Diaz-Buxo, CCPD Technique and Current Clinical Experience (1982).

Diaz-Buxo, et al., Continuous Cyclic Peritoneal Dialysis: A Preliminary Report, Artificial Organs, vol. 5, No. 2, pp. 157-161 (May 1981).

Diaz-Buxo, Current Status of Continuous Cyclic Peritoneal Dialysis (CCPD), Peritoneal Dialysis International, vol. 9, pp. 9-14 (1989).

Diaz-Buxo, Issues in Nephrology: Continuous Cyclic Peritoneal Dialysis, NAPHT News, Feb. 1983, pp. 12-14.

Diaz-Buxo, Peritoneal Dialysis Reverse Osmosis Machines and Cyclers, Dialysis Therapy, pp. 41-48 (1986).

Drukker et al., Replacement of Renal Function by Dialysis, 2nd Ed., Ch. 21, 1983.

Lewin and Maxwell, Sorbent-Based Regenerating Peritoneal Dialysis, Sorbents and Their Clinical Applications, pp. 353-374 (1980).

Lewin et al., Sorbent for Application in the Treatment of ESRD Patients, Annual Progress Report re Contract #N01-AM-9-2215, submitted Jun. 22, 1982.

Ratnu, et al., A New Technique—Semicontinuous Rapid Flow, High Volume Exchange—for Effective Peritoneal Dialysis in Shorter Periods, Nephron, vol. 31, pp. 159-163 (1982).

Twardowski, Peritoneal Dialysis: Current Technology and techniques, Postgraduate Medicine, vol. 85, No. 5 (Apr. 1989).

Product Evaluation Reports: Peritoneal Dialysis Machine "Pac-X," Hospital Materials Management, vol. 12, No. 11, p. 16 (Nov. 1987).

Brochure entitled, AP Hauni: Automatisches Peritonealdialyse-Great (1970).

Brochure entitled, Fresenius Delivers 90/2 Peritoneal Therapy Cycler.

Brochure entitled, REDY Universal Re-circulating Dialysate System.
Brochure entitled, SIF 901 Perugia.
Translation of brochure entitled, SIF 901 Perugia.
Translation of Certificate for translation of brochure entitled, SIF 901 Perugia.
Operators Instructions for Fresenius 90/2 Peritoneal Therapy Cycler.
Photo of dialysis patient connected to machine.
Photo of dialysis machine.
Peritoneal Dialyser PD700 Service Manual, Jun. 1977.
Peritoneal Dialyser PD700 Instruction Manual.
PD700 Peritoneal Dialyser Users Hand-book, Dec. 1977.
Operating Instructions, Peritoneal Dialyser PD700, For Ser. No. 300.
Brochure entitled, Peritoneal Dialyser PD700, May 1979.
Brochure entitled, For Volume Measurement, Temperature Control and Cycling of Dialysing Fluid, Peritoneal Dialyser PD700, 1970.
Skotselanvisning for Peritoneal—Dialysapparat PD700.
Bergstrom et al., An Automated Apparatus for Peritoneal Dialysis with Volumetric Fluid Balance Measurement, reprinted from Dialysis & Transplantation, Jun./Jul. 1976.
U. Callsen, Peritoneal-Dialysator PD700, Prakt. Anasth. 9 (1974).
Piazolo et al., Erfahrungen mit einem neuen vollautomatsischen Paritoneal-dialysegerat, Munchener Medizinische Wochenschrift, 1972.
Technical Note, PD700 Peritoneal Dialyser, Jan. 29, 1979.
Assorted Photos of dialysis machine with and without casing on.
Elsevier Science Ltd., Air-Operated Diaphragm Pumps, World Pumps, Jan. 1996, at 38.
Bran & Luebbe GmbH, Diaphragm Metering Pumps, Chem. Eng'g Progress, Apr. 1987, at 18-24.
M. Schalbach, E.S. Bucherl & O. Franke, An Electronically Controlled Implantable Auxiliary Ventricle, published in Advances in Biomedical Engineering and Medical Physics: Cardiac Engineering, vol. 3.
Gene L. Mrava, Mock Circulation Systems for Artificial Hearts, published in Advances in Biomedical Engineering and Medical Physics: Cardiac Engineering, vol. 3.
W.M. Phillips, J.A. Brighton & W.S. Pierce, Artificial Heart Evaluation Using Flow Visualization Techniques, published in Transactions: American Society for Artificial Internal Organs, vol. XVIII (1972).
J.A. Brighton, W.S. Pierce, D.Landis & G. Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).
Operator's Instructions, Fresenius 90/2 Peritoneal Therapy Cycler (Rev. C. copyright 1991-2000).
Memorandum of Donald X. Vaccarino entitled 90/2 History File (1991-1992).
Document entitled 90/2 Cycler Software, Version 3.96 (Jan. 24, 1992).
Software Change Requests (Jul. 8, 1991-Oct. 3, 1992).
Brochure entitled Fresenius Delivers 90/2 Peritoneal Therapy Cycler (Apr. 2001).
90/2 Quick Reference.
90/2 Cycler Parts List (Nov. 6, 1997).
90/2 Cycler Box Contents.
90/2 Brochure (Jul. 1993).
90/2 Brochure (Apr. 2001).
90/2 Directions for Use.
90/2 Document Index.
Freedom Cycler Document Index.
Specification entitled Inpersol Cycler 3000 Operating Manual, List No. 21952-04, dated 1990.
Training aid entitled Learning to Use the Inpersol Cycler 3000, dated Jul. 1991.
Fresenius USA/Delmed 90/2 Peritoneal Dialysis System Operators Manual, dated Feb. 6, 1991.
Fresenius 90/2 Peritoneal Therapy Cycler Operator's Instructions, dated 2000.
Fresenius 90/2 PD Cycler Set Patient Information Card.
Fresenius Freedom Cycler Operating Instructions.
Opening Expert Witness Report of Dr. Juan Santiago Regarding Anticipation and Obviousness of the Claims of U.S. Patents Nos. 6,503,062 and 6,808,369 in view of the Prior Art and based on the Indefiniteness, Lack of Enablement, and Lack of Written Description of Certain Claims of U.S. Patent Nos. 6,503,062 and 6,808,369, Apr. 24, 2009.
Opening Expert Witness Report of William K. Durfee Regarding whether Certain Claims of U.S. Patent No. 5,324,422, U.S. Patent No. 5,421,823, U.S. Patent No. 5,431,626 and U.S. Patent No. 5,438,510 were Ready for Patenting, Apr. 24, 2009.
Expert Witness Report of Fred K. Forster: Analysis of Obviousness of Certain Asserted Claims of U.S. Patent Nos. 5,431,626; 5,324,422; and 5,438,510, Apr. 24, 2009.
Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.
Exhibit A, Credentials of Ronald J. Adrian.
Exhibit B, Materials Considered by Ronald J. Adrian.
Expert Report on Development of the PD700 and Motivation to Combine the PD700 and U.S. Patent No. 5,088,515, Sven Olofsson, Apr. 24, 2009.
Expert Witness Report of Juan G. Santiago Regarding Lack of Written Description, Non-Enablement, and Indefiniteness of the Asserted Claims of U.S. Patent Nos. 5,421,823; 5,324,422; 5,438,510; and 5,431,626, Apr. 24, 2009.
Opening Expert Witness Report of Dr. Martin Roberts Regarding a History of Peritoneal Dialysis and the Obviousness and Consequent Invalidity of the Asserted Claims of U.S. Patent No. 5,421,823, Apr. 24, 2009.
Opening Expert Witness Report of Dr. Darrell Long Regarding Technical Features of the High Flow Peritoneal Dialysis and Personal Cycler Machines, Apr. 24, 2009.
Non-Final Office Action for U.S. Appl. No. 10/155,754 mailed Sep. 11, 2003.
Final Office Action for U.S. Appl. No. 10/155,754 mailed Mar. 24, 2004.
Non-Final Office Action for U.S. Appl. No. 11/614,850 mailed May 13, 2009.
Final Office Action for U.S. Appl. No. 11/614,850 mailed Mar. 18, 2010.
Non-Final Office Action for U.S. Appl. No. 11/614,858 mailed May 13, 2010.
Non-Final Office Action for U.S. Appl. No. 11/617,527 mailed Nov. 24, 2008.
Final Office Action for U.S. Appl. No. 11/617,527 mailed May 5, 2009.
Non-Final Office Action for U.S. Appl. No. 11/617,527 mailed Aug. 12, 2009.
Final Office Action for U.S. Appl. No. 11/617,527 mailed Jan. 21, 2010.
Non-Final Office Action for U.S. Appl. No. 11/617,527 mailed Jul. 16, 2010.
Non-Final Office Action for U.S. Appl. No. 10/446,068 mailed May 12, 2006.
Final Office Action for U.S. Appl. No. 10/446,068 mailed Nov. 7, 2006.
Non-Final Office Action for U.S. Appl. No. 10/446,068 mailed Sep. 7, 2007.
Final Office Action for U.S. Appl. No. 10/446,068 mailed Feb. 28, 2008.
Final Office Action for U.S. Appl. No. 10/446,068 mailed Jul. 31, 2008.
Non-Final Office Action for U.S. Appl. No. 10/446,068 mailed Nov. 14, 2008.
Non-Final Office Action for U.S. Appl. No. 11/773,787 mailed Jul. 28, 2010.
Non-Final Office Action for U.S. Appl. No. 12/506,738 mailed Jun. 24, 2011.
Non-Final Office Action for U.S. Appl. No. 12/903,902 mailed Jul. 6, 2011.
Non-Final Office Action for U.S. Appl. No. 12/903,887 mailed Jul. 6, 2011.

Non-Final Office Action for U.S. Appl. No. 11/773,148 mailed May 17, 2010.
Final Office Action for U.S. Appl. No. 11/773,148 mailed Feb. 7, 2011.
Non-Final Office Action for U.S. Appl. No. 11/617,543 mailed Sep. 24, 2007.
Final Office Action for U.S. Appl. No. 11/617,543 mailed May 30, 2008.
Non-Final Office Action for U.S. Appl. No. 11/617,543 mailed Oct. 20, 2008.
Final Office Action for U.S. Appl. No. 11/617,543 mailed Jul. 22, 2009.
Non-Final Office Action for U.S. Appl. No. 12/987,738 mailed Apr. 29, 2011.

* cited by examiner

SYSTEM FOR MONITORING AND CONTROLLING PERITONEAL DIALYSIS

PRIORITY CLAIM

This application claims priority to and the benefit of a continuation of U.S. patent application Ser. No. 10/446,068, filed May 27, 2003, which is a divisional application of U.S. patent application Ser. No. 10/078,568, filed Feb. 14, 2002, issued as U.S. Pat. No. 6,592,542, which is a continuation of U.S. patent application Ser. No. 09/501,778, filed Feb. 10, 2000, issued as U.S. Pat. No. 6,497,676.

BACKGROUND

The present invention relates generally to the treatment of end stage renal disease. More specifically, the present invention relates to methods and apparatus for monitoring the performance of peritoneal dialysis.

Using dialysis to support a patient whose renal function has decreased to the point where the kidneys no longer sufficiently function is known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, certain inherent disadvantages exist with hemodialysis.

To overcome the disadvantages associated with hemodialysis, peritoneal dialysis was developed. Peritoneal dialysis utilizes the patient's own peritoneum as a semi-permeable membrane. The, peritoneum is a membranous lining of the abdominal body cavity. Due to good perfusion, the peritoneum is capable of acting as a natural semi-permeable membrane.

Peritoneal dialysis periodically infuses sterile aqueous solution into the peritoneal cavity. This solution is called peritoneal dialysis solution, or dialysate. Diffusion and osmosis exchanges take place between the solution and the blood stream across the natural body membranes. These exchanges remove the waste products that the kidneys normally excrete. The waste products typically consist of solutes like urea and creatinine. The kidneys also maintain the levels of other substances such as sodium and water which need to be regulated by dialysis. The diffusion of water and solutes across the peritoneal membrane during dialysis is called ultrafiltration.

In continuous ambulatory peritoneal dialysis, a dialysis solution is introduced into the peritoneal cavity utilizing a catheter. An exchange of solutes between the dialysate and the blood is achieved by diffusion. Further removal is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter.

Peritoneal dialysis raises a number of concerns including: the danger of peritonitis; a lower efficiency and therefore increased duration of dialysis hours compared to hemodialysis; and costs incurred when automated equipment is utilized.

A number of variations on peritoneal dialysis have been explored. One such variation is automated peritoneal dialysis ("APD"). APD uses a machine, called a cycler, to automatically infuse, dwell, and drain peritoneal dialysis solution to and from the patient's peritoneal cavity. APD is particularly attractive to a peritoneal dialysis patient, because it can be performed at night while the patient is asleep. This frees the patient from the day-to-day demands of continuous ambulatory peritoneal dialysis during his/her waking and working hours.

The APD sequence typically lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. APD can be and is practiced in a number of different ways.

Current APD systems do not monitor the patient intraperitoneal pressure during a therapy session. Current systems simply limit the external pressure (or suction) that a pump can apply to the line or lumen that is attached to the patient catheter. If the patient is located below the system, sometimes referred to as a cycler, a gravity head will add to the positive fill pressure that the cycler can apply to the patient catheter. Conversely, if the patient is located above the cycler, the gravity head will decrease from the positive fill pressure that the cycler can apply to the patient catheter.

The monitoring of intraperitoneal pressure would be useful because cyclers will sometimes not fully drain a patient between cycles. Specifically, currently-available cyclers are unable to determine whether a patient absorbed some fluid or whether some fluid is simply not able to be drained out because of the position of the patient or the catheter.

As a result, some currently-available systems utilize a minimum drain threshold to determine the amount of fluid that should be delivered to the patient during the next fill. For example, if 85% of the fill volume has been drained when the cycler determines that the patient is "empty", the next fill volume will be 100%. If only 80% were drained, the next fill volume would be limited to 95%.

A negative ultrafiltrate (uF) alarm will sound when the patient has retained more than a predetermined percentage of the fill volume. The predetermined percentage can typically be either 50% or 100% of the fill volume. However, the patient can override this alarm if he/she does not feel overfull. The number of times the patients can override the uF alarm during a single therapy may be limited by the software of the cycler. However, the uF alarm typically does not consider the actual ultrafiltrate that may also accumulate in the peritoneal cavity along with the dialysate.

Currently-available cyclers fill the patient to a specific, preprogrammed volume during each cycle. The doctor prescribes this fill volume based upon the patient's size, weight and other factors. However, because currently-available cyclers cannot monitor intraperitoneal pressure, the doctor cannot take this factor into account when formulating the prescription. It is also known that intraperitoneal pressure (IPP) has an effect on ultrafiltration (UF).

FIGS. 1-3 provide schematic illustrations of current APD cyclers. None of them attempt to monitor intraperitoneal pressure.

Referring to FIG. 1, a cycler 10a is illustrated which includes a dialysate container 11, a patient 12 and a drain container 13 are illustrated schematically. The infusion of dialysate from the container 11 into the patient 12 is caused by the gravitational head indicated at 14 while the draining of used dialysate from the patient 12 to the drain container 13 is caused by the drain head indicated at 15. The cycler 10a includes no sensors for monitoring the pressure inside the peritoneum of the patient 12. A single lumen 16 connects both the dialysate container 11 and drain container 13 to the patient 12. Valves 17, 18 operated by the cycler 10a control the flow of either dialysate from the container 11 to the patient 12 or waste material from the patient 12 to the drain container 13.

Turning to FIG. 2, in the cycler 10b, the drain container 13 and dialysate container 11 are contained within a pressurized chamber 19. The chamber 19 can be pressurized or evacuated to either fill or drain the patient. Again, the selective operation of valves 17, 18 control whether dialysate is being transferred to or from the patient 12. Again, no sensors are provided for detecting or monitoring intraperitoneal pressure of the patient 12.

Turning to FIG. 3, in the system 10c, a dialysate container 11 is connected to a pump 21 which, in turn, connects the dialysate container 11 to a common lumen or catheter 16 which is connected to the patient. A fluid flow control valve is provided at 23 and is controlled by the cycler 10c. The drain container 13 is also connected to a pump 24 which, in turn, connects the drain container 13 to the lumen 16. A control valve is again provided at 25.

The drain and fill rates of the cyclers 10a-10c illustrated in FIGS. 1-3 are determined by the gravitational head (see FIG. 1) or the suction or pressure (see FIGS. 2 and 3) applied to the patient line 16. Typically, the cyclers 10a-10c fail to optimize either the fill rate or the drain rate because the pressure is either fixed by the gravitational head or the pressure or suction applied by the chamber 10b of FIG. 2 which occurs at the opposing end of the patient line 16. Thus, without measuring the intraperitoneal pressure or having a way to estimate the same, it is difficult to optimize either the drain or fill rate. In the case of the cycler 10c in FIG. 3, optimizing the drain or fill rate is guesswork due to the lack of any pressure reading at all.

Accordingly, there is a need for an improved cycler that measures patient intraperitoneal pressure during a therapy session, including both during the drain and the fill as well as the dwell. Further, there is a need for an improved cycler that measures intraperitoneal pressure and which would use that data to more completely drain a patient between cycles. Further, there is a need for an improved cycler which would accurately measure intraperitoneal pressure to avoid overfilling a patient. Finally, there is a need for an improved cycler which would monitor intraperitoneal pressure during both the fill and drain cycles to optimize the speed at which the patient is filled and drained and to therefore increase the dwell portion of a therapy session.

SUMMARY

The present invention satisfies the aforenoted needs by providing a system for providing peritoneal dialysis to a patient which comprises a dialysate container connected to the patient with a first pressure sensor connected in-line therebetween, and a drain container connected to the patient with a second pressure sensor connected in-line therebetween.

In an embodiment, the system further comprises a first pump disposed in-line between the dialysate container and the first pressure sensor.

In an embodiment, the dialysate flows from the dialysate container into the patient under a hydrostatic head.

In an embodiment, a second pump is disposed in-line between the drain container and the second pressure sensor.

In an embodiment, the dialysate flows from the patient to the drain container under a hydrostatic head.

In an embodiment, the second pressure sensor measures an intraperitoneal pressure of the patient while dialysate flows from the dialysate container to the patient.

In an embodiment, the first pressure sensor measures an intraperitoneal pressure of the patient while dialysate flows from the patient to the drain container.

In an embodiment, the system further comprises a first lumen connecting the dialysate container to the first sensor and the first sensor to a catheter, and a second lumen connecting the drain container to the second sensor and the second sensor to the catheter, the catheter being connected to the patient, a flow of dialysate from the patient to the drain container evacuating dialysate from the first lumen and causing said dialysate from the first lumen to flow through the second lumen and to the drain container.

In an embodiment, the catheter is a dual lumen catheter.

In an embodiment, the first and second sensors are redundant in-line pressure/vacuum sensors.

In an embodiment, the present invention provides a method for dialyzing a patient comprising the steps of: placing a catheter in a peritoneum of the patient; providing at least one dialysate container; connecting the dialysate container to the catheter with a first lumen that includes a first pressure sensor disposed in-line and between the catheter and the dialysate container; providing at least one drain container; connecting the drain container to the catheter with a second lumen that includes a second pressure sensor disposed in-line and between the catheter and the drain container; transferring dialysate from the dialysate container to the peritoneum of the patient and monitoring an intraperitoneal pressure of the patient with the second pressure sensor; and transferring dialysate from the peritoneum of the patient to the drain container and monitoring the intraperitoneal pressure of the patient with the first pressure sensor.

In an embodiment, the step of transferring dialysate from the dialysate container to the peritoneum of the patient further comprises pumping dialysate from the dialysate container to the patient with a first pump disposed in-line between the dialysate container and the first pressure sensor.

In an embodiment, the step of transferring dialysate from the peritoneum of the patient to the drain container further comprises pumping dialysate from the peritoneum of the patient to the drain container with a second pump disposed in-line between the drain container and the second pressure sensor.

In an embodiment, the dialysate container is disposed vertically above the peritoneum of the patient and the step of transferring dialysate from the dialysate container to the peritoneum of the patient further comprises flowing dialysate from the dialysate container to the patient under a hydrostatic head.

In an embodiment, the drain container is disposed vertically below the peritoneum of the patient and the step of transferring dialysate from the peritoneum of the patient to the drain container further comprises flowing dialysate from the peritoneum of the patient to the drain container under a hydrostatic head.

Additional features and advantages are described herein, and will be apparent from the following Detailed Description and the figures.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

Figure 1:
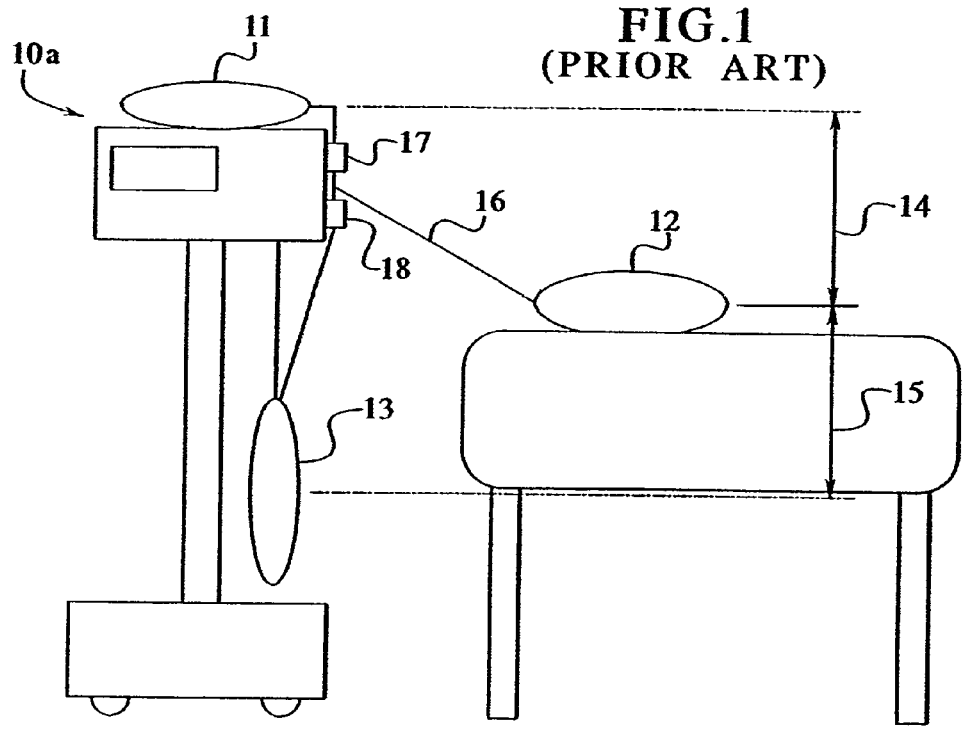
FIG. 1 illustrates, schematically, a prior art automated peritoneal dialysis system.
Figure 2:
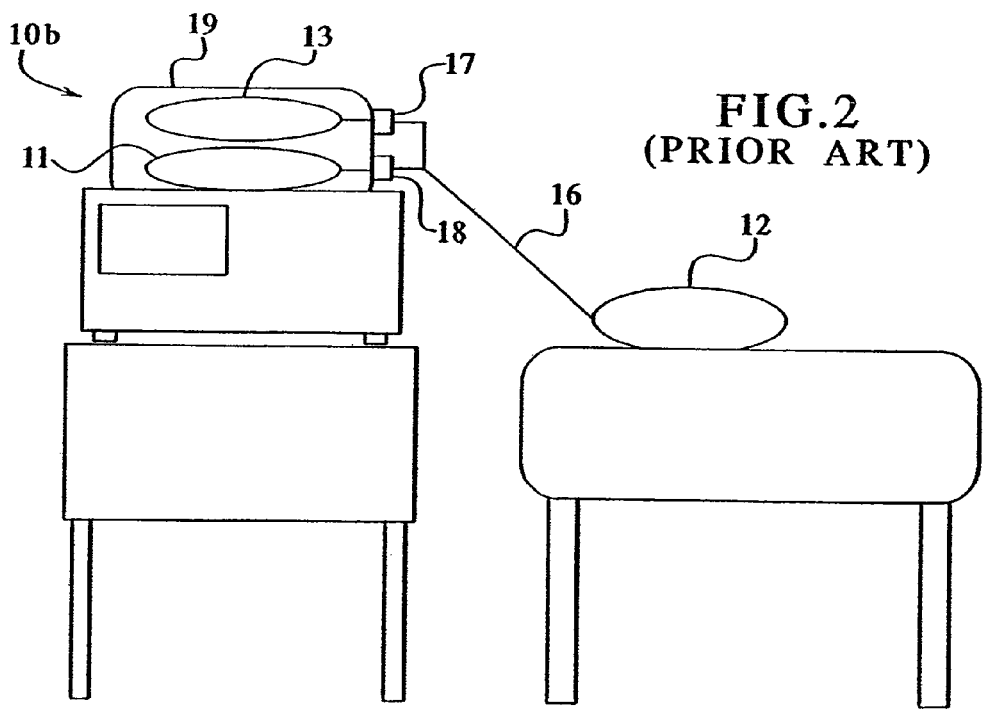
FIG. 2 illustrates, schematically, a prior art automated peritoneal dialysis system.
Figure 3:
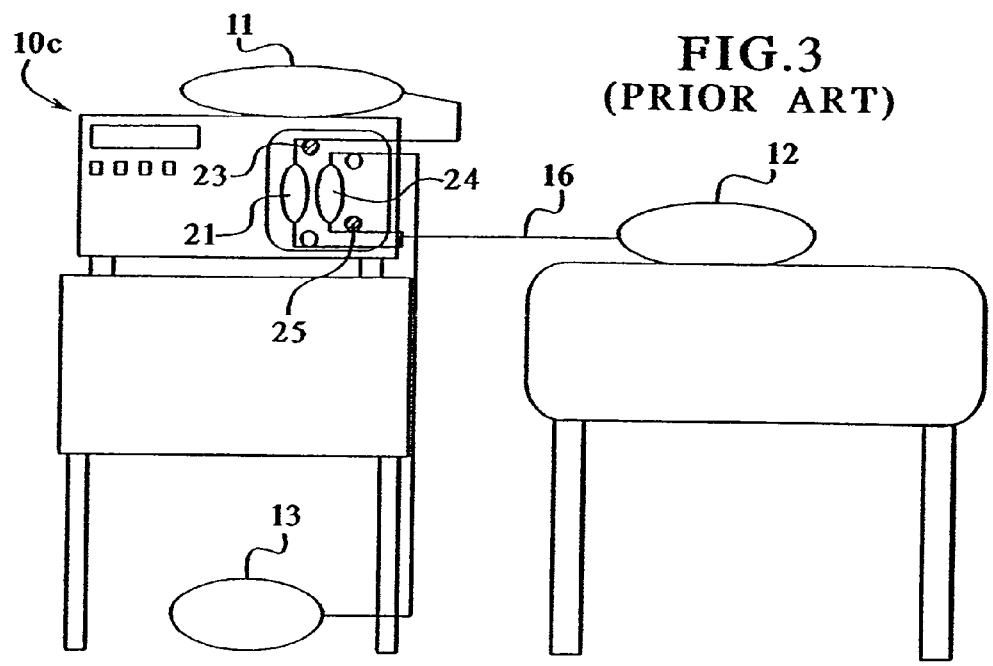
FIG. 3 illustrates, schematically, a prior art automated peritoneal dialysis system.
Figure 4:
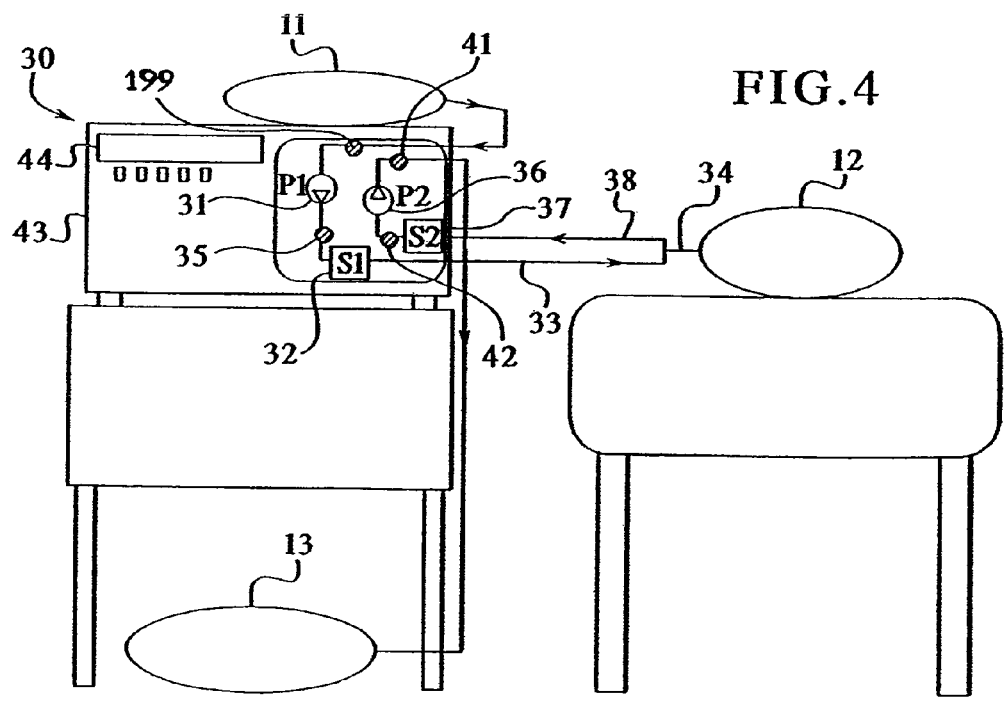
FIG. 4 illustrates, schematically, an automated peritoneal dialysis system made in accordance with the present invention.

Turning to FIG. 4, a cycler 30 includes a dialysate container 11 connected to a pump 31. The pump 31 is connected to a pressure sensor 32. The pump 31 and pressure sensor 32 are disposed in-line in a lumen 33 that connects the dialysate container 11 to a catheter 34. Control valves are provided at 35, 199. A drain container 13 is also connected to a pump 36 which is connected to a sensor 37. The pump 36 and sensor 37 are also connected in-line to a lumen 38 which connects the drain container 13 to the catheter 34. Control valves are again provided at 41, 42. During the fill, the pump 31 pumps dialysate from the container 11 through the lumen 33 and catheter 34 into the peritoneum (not shown) of the patient 12. During this time, the sensor 37 monitors and measures the intraperitoneal pressure. A signal is sent to the controller of the cycler 30 shown schematically at 43. A control panel is indicated generally at 44.

During the drain, the sensor 32 can accurately monitor and measure the intraperitoneal pressure of the patient 12. In the embodiment illustrated in FIG. 4, no pumps or control valves are disposed between the sensor 32 and the patient 12.

Figure 5:
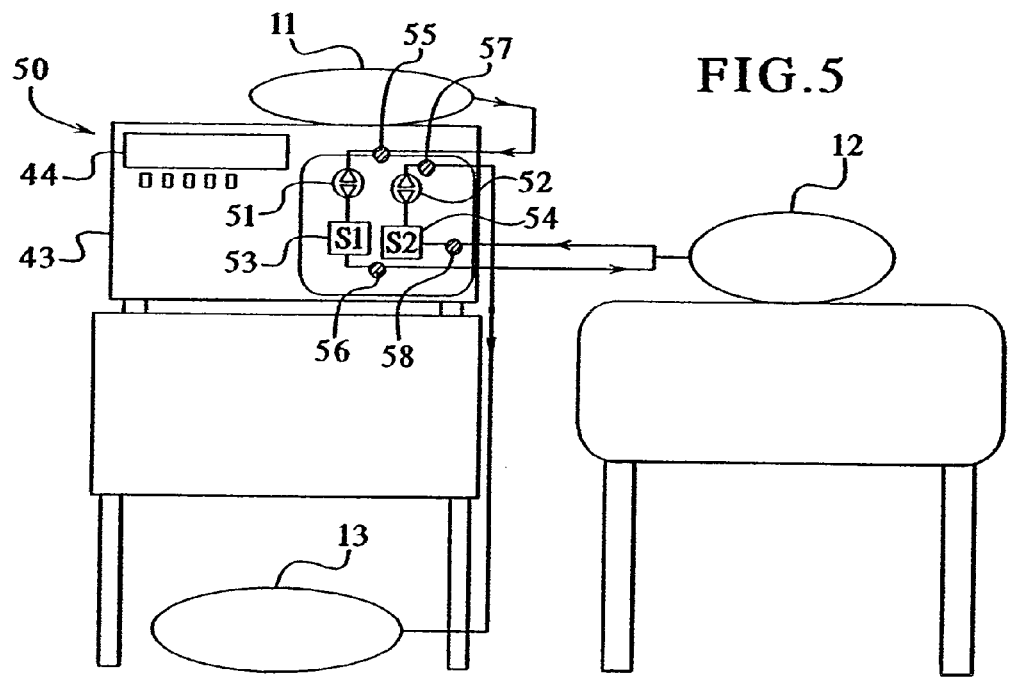
FIG. 5 illustrates, schematically, a second embodiment of an automated peritoneal dialysis system made in accordance with the present invention.

Turning to FIG. 5, a cycler 50 is illustrated which includes reversible pumping chambers 51, 52 with sensors 53, 54 disposed between the reversible pumping chambers 51, 52 and the patient 12 respectively. Control valves 55 and 56 are disposed on another side of the reversible pumping chamber 51 and the sensor 53 and control valves 57, 58 are provided on either side of the reversible pumping chamber 52 and sensor 54. The sensors 53, 54 actually measure the pressure on the diaphragms of the reversible pumping chambers 51, 52.

Figure 6:
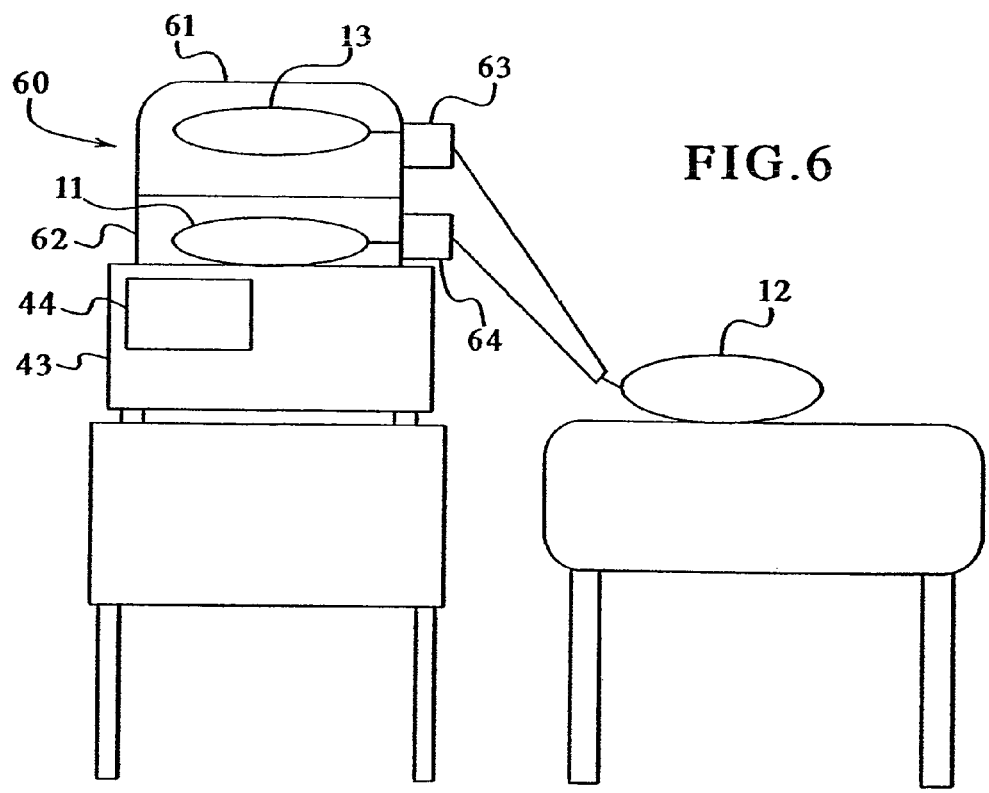
FIG. 6 illustrates, schematically, a third embodiment of an automated peritoneal dialysis system made in accordance with the present invention.

Turning to FIG. 6, a cycler 60 is illustrated with a chamber 61 for accommodating the drain container 13 and a chamber 62 for accommodating the dialysate container 11. Each chamber 61, 62 is equipped with an integrated valve assembly and pressure sensor shown at 63, 64. In the embodiment 60 shown in FIG. 6, the chamber 61 must be capable of being evacuated. Dialysate may flow from the dialysate container 11 by way of gravity or pressure fill. Again, the sensors of the valve assembly/sensor combinations 63, 64 monitor the intraperitoneal pressure of the patient 12 as discussed above.

Figure 7:
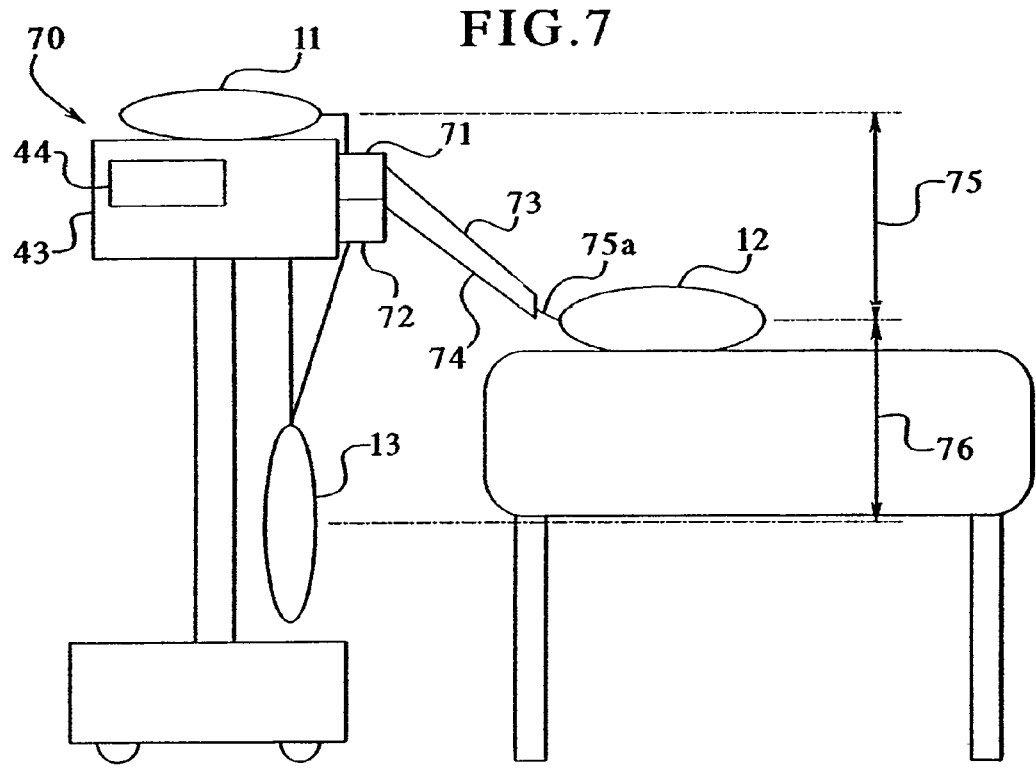
FIG. 7 illustrates, schematically, a fourth embodiment of an automated peritoneal dialysis system made in accordance with the present invention.

In the embodiment 70 illustrated in FIG. 7, the dialysate container 11 and drain container 13 are both connected to integrated control valves and pressure sensors 71, 72. Each of the integrated control valves and pressure sensors 71, 72 are connected to lumens 73, 74 respectively which are connected to the catheter 75a by way of a Y-connection. The details of all the Y-connections and clamps are not shown but are known to those skilled in the art. Flow from the dialysate container 11 to the patient is carried out under the gravitational head shown at 75 while flow from the patient to the drain container 13 is carried out under the gravitational head shown at 76.

Figure 8:
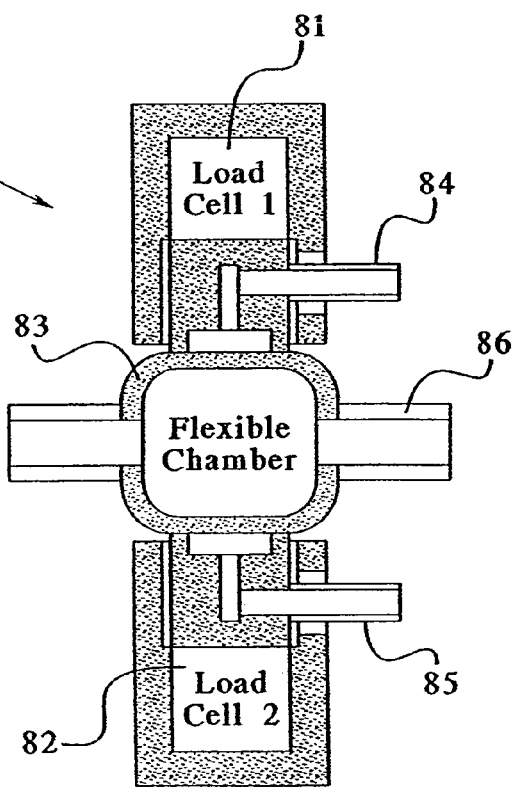
FIG. 8 illustrates a pressure sensor made in accordance with the present invention.

FIG. 8 illustrates one in-line pressure sensor 80 that is suitable for use with the present invention. Redundant load cells 81, 82 are connected to the flexible pressure sensing membrane 83 by a vacuum connected by the line 84, 85. A lumen connecting the cycler to the patient is shown at 86.

Figure 9:
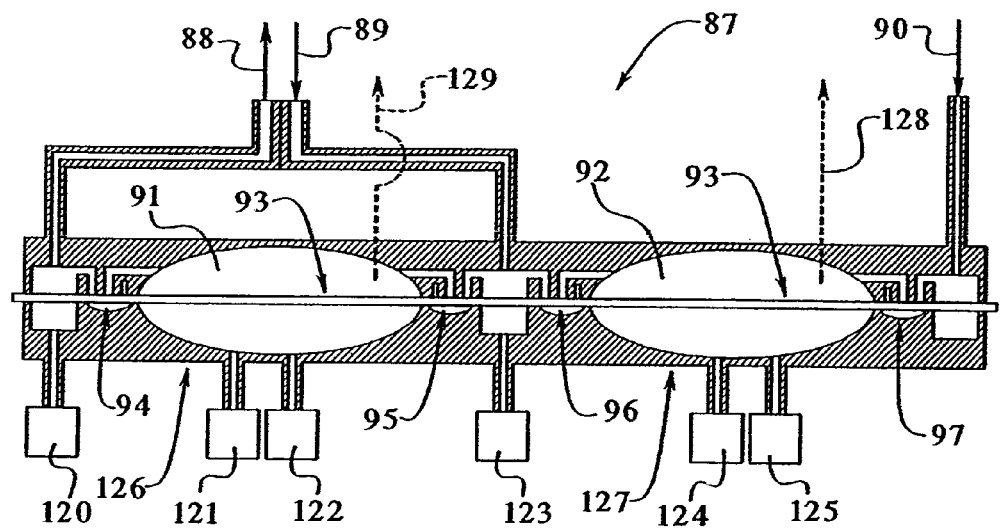
FIG. 9 illustrates a fifth embodiment incorporating dual pumping chambers and pressure sensors made in accordance with the present invention.

FIG. 9 illustrates a dual-pumping chamber cassette 87 which includes an output line 88 which connects the cassette 87 to the patient and an input line 89 connecting the patient to the cassette 87. The line 90 connects the cassette 87 to the dialysate container (not shown). Each pumping chamber 91, 92 are in communication with all three lines 88, 89 and 90. Thus, every line can be connected to either pumping chamber 91, 92. The pumping chambers 91, 92 are bound on one side by a common diaphragm shown at 93. Flow is controlled by the use of diaphragm valves shown at 94, 95, 96 and 97. Pressure sensors are shown at 120, 121, 122, 123, 124, 125. However, pressure sensors 123 and 120 are the sensors used to measure intraperitoneal pressure in accordance with the present invention. The remaining sensors 121, 122, 124, 125 are used to monitor the operation of the pumps 126, 127.

When the left diaphragm pump 126 is pushing dialysate to the patient, the sensor 123 can measure the intraperitoneal pressure through the line 89. When the left diaphragm pump 126 is draining fluid from the patient through the line 89, the sensor 120 can measure intraperitoneal pressure through the line 88 and while the right pump 127 is pumping fluid to the drain container (not shown) through the drain line shown schematically at 128. When the right diaphragm pump 127 is being used to drain fluid from the patient, the sensor 120 can measure intraperitoneal pressure while the left diaphragm pump 126 is pumping fluid to the drain container (not shown) through the drain line shown schematically at 129.

Figure 10:
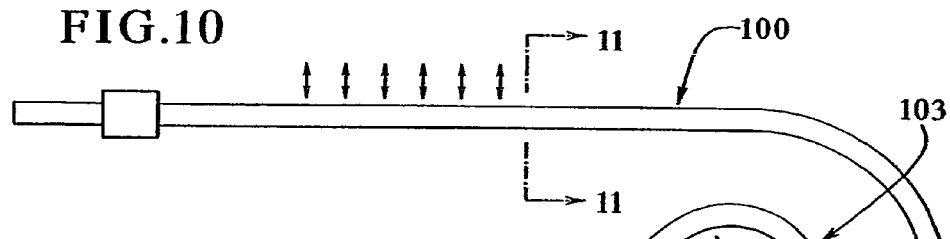
FIG. 10 illustrates, schematically, a dual lumen catheter that can be utilized with the present invention.
Figure 11:
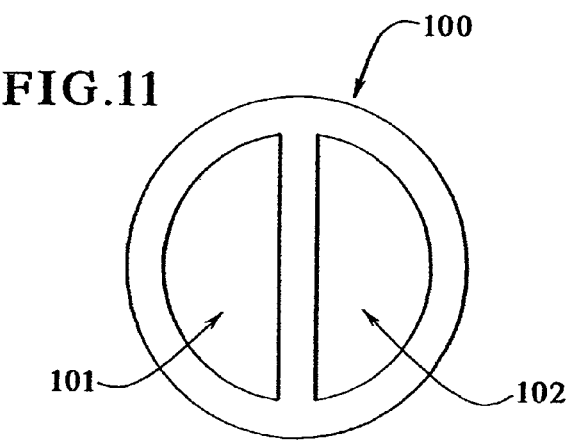
FIG. 11 is a sectional view taken substantially along line 11-11 of FIG. 10.

FIGS. 10 and 11 illustrate a dual-lumen catheter 100 which includes separate passageways 101, 102. The employment of a dual lumen catheter 100 as compared to a dual lumen patient line can move the point at which the pressure is measured to within the peritoneum itself by way of communication through the separate flowpaths 101, 102. The dual lumen catheter 100 installs like a single lumen catheter, yet will function either as a flow through or a standard catheter. Both fluid pathways 101, 102 are used to withdraw and deliver fluid during the drain and fill. While one pathway delivers fluid, the other pathway drains. The end section, shown generally at 103, is perforated.

A comparison of an APD therapy for a prior art APD cyclers and one manufactured in accordance with the present invention are summarized as follows:

| Therapy Parameter | Current APD Cycler | Cycler Using Invention |
|---|---|---|
| Total Therapy Volume | 15 liters | 15 liters |
| Fill Volume | 2.2 liters | 2.5 liters max |
| Fill Pressure Limit | not applicable | 14 mm Hg max |
| Total Therapy Time | 8 hours | 8 hours |
| Last (Day) Fill Volume | 1,500 ml | 1,500 ml |
| Last Fill Dextrose | Same | Same |
| Initial Drain Alarm | 1,200 ml | 1,200 ml |
| Drain X of N Alarm | 80% | 80% |

TABLE 1

Comparison of Therapies for Current Cylcers versus Cycler using Invention Method

| Therapy Phase | Therapy Parameter | Prior Art Cycler 1 | Prior Art Cycler 2 | Invention Cycler 3 |
|---|---|---|---|---|
| Initial Drain | Drain Volume | 1,200 ml | 1,200 ml | 1,200 ml |
|  | Patient Volume | 300 ml | 300 ml | 300 ml |
| Fill 1 of 5 | Fill Volume | 2,200 ml | 2,200 ml | 2,500 ml |
|  | Patient Volume | 2,500 | 2,500 | 2,800 |
|  | Fill Pressure | not applicable | not applicable | 12 mm Hg |
| Drain 1 of 5 | Drain Volume | 1,800 ml | 2,200 ml | 2,200 ml |
|  | Patient Volume | 700 ml | 300 ml | 600 ml |
| Fill 2 of 5 | Fill Volume | 2,200 ml | 2,200 ml | 2,400 ml |
|  | Patient Volume | 2,900 ml | 2,500 ml | 3,000 ml |
|  | Patient Pressure | not applicable | not applicable | 14 mm Hg |
| Drain 2 of 5 | Drain Volume | 1,800 ml | 2,200 ml | 2,200 ml |
|  | Patient Volume | 1,100 ml | 300 ml | 800 ml |
| Fill 3 of 5 | Fill Volume | 2,200 ml | 2,200 ml | 2,200 ml |
|  | Patient Volume | 3,300 ml | 2,500 ml | 3,000 ml |
|  | Patient Pressure | not applicable | not applicable | 14 mm Hg |
| Drain 3 of 5 | Drain Volume | 1,801 ml | 2,200 ml | 2,200 ml |
|  | Patient Volume | 1,499 ml | 300 ml | 800 ml |
| Fill 4 of 5 | Fill Volume | 2,200 ml | 2,200 ml | 2,200 ml |
|  | Patient Volume | 3,699 ml | 2,500 | 3,000 ml |
|  | Patient Pressure | not applicable | not applicable | 3,000 ml |
| Drain 4 of 5 | Drain Volume | 1,800 ml | 2,200 ml | 2,200 ml |
|  | Patient Volume | 1,899 ml | 300 ml | 800 ml |
| Fill 5 of 5 | Fill Volume | uF Alarm Bypass 2,200 ml | 2,200 ml | 2,200 ml |
|  | Patient Volume | 4,099 ml | 2,500 ml | 3,000 ml |
|  | Patient Pressure | Patient Wakes Overfull, Manually Drains 1,500 ml | not applicable | 14 mm Hg |
| Drain 5 of 5 | Drain Volume | 1,800 ml | 2,200 ml | 2,200 ml |
|  | Patient Volume | 799 ml | 300 ml | 800 ml |
| Final Fill | Fill Volume | 1,500 ml | 1,500 ml | 1,500 ml |

Inspection of Table 1 shows that cycler 1 woke the patient at around 4:30 in the morning with a negative uF alarm at the beginning of Fill 5. The patient bypassed the alarm because he did not feel overfull and immediately fell back asleep. He woke up about 15 minutes later when he had difficulty breathing and felt extremely overfull. He manually drained about 1500 ml but was unable to go back to sleep. He filed a formal product complaint with the manufacturer.

The data of Table 1 shows that cycler 2 ran a completely normal therapy but the total therapy clearance (calculated based upon the sum of the night patient volumes) was only 84.5% of that obtained by cycler 3, which was using the cycler that used the method of the current invention.

The data of Table 1 shows that cycler 3 ran a completely normal therapy and that the fill volume was limited on one occasion by the maximum fill volume but on four occasions by the patient's intraperitoneal pressure. This patient never felt any discomfort and had no alarms during the night. The limit on the IPP prevented him from being overfilled even though he had successive drains that were not complete. The volume of fluid in his peritoneum never exceeded 3 liters.

The patient on cycler 1 had an intraperitoneal pressure in excess of 14 mm Hg during dwells 3 and 4. His breathing may have been impaired and his heart may have had to work harder but the discomfort was not enough to wake him up from a sound sleep until it peaked at 4,099 ml during dwell 5.

In conclusion, the method of the present invention provides for optimum fills and therefore more clearance while preventing overfills that bring discomfort and inhibit the function of vital body organs. A negative uF alarm would seldom occur because overfills of the required magnitude would be prevented by the IPP sensors.

Calculation of Intraperitoneal Pressure (IPP)

In order to calculate the IPP, one may first calculate the patient head height correction using conservation of energy:

$$\Delta(\tfrac{1}{2}\rho V^2 + P - \rho a_g h) + \text{Frictional Losses} = 0$$

The velocity V of fluid through the patient line is the same at both ends of the line as is the fluid density, so this equation can be written as $$(P_2 - P_1) - \rho a_g (h_2 - h_1) + \text{Frictional Losses} = 0$$

which can be rearranged as $$\Delta h = \frac{(P_1 - P_2) - \text{Frictional Losses}}{\rho a_g}$$

EXAMPLE 1

P1=1.25 psig=85060 (gram/cm)/(cm$^2$-sec$^2$)
P2=0.9 psig=61240 (gram/cm)/(cm$^2$-sec$^2$)
Frictional Losses=39130 (gram/cm)/(cm$^2$-sec$^2$) with flow of 197 cmn/min in a 4 mm ID line at a velocity of approximately 172 cm/sec, wherein
  $a_g$ 981 cm/sec$^2$
  $\rho$=1 gram/cm$^3$ $$\Delta h = \frac{((85060 - 61240) - 39130)(\text{gram/cm})(\text{cm}^2 - \text{sec}^2)}{1 \text{gram/cm}^3 * 981 \text{cm/sec}^2}$$

$\Delta h$=−15.6 cm (The patient is 15.6 cm below the membrane)

EXAMPLE 2

P1=1.25 psig=85060 (gram/cm)/(cm$^2$-sec$^2$)
P2=0.45 psig=30620 (gram/cm)/(cm$^2$-sec$^2$)
Frictional Losses=39130 (gram/cm)/(cm$^2$-sec$^2$) with flow of 197 cmn/min in a 4 mm ID line at a velocity of approximately 172 cm/sec, wherein
  $a_g$=981 cm/sec$^2$
  $\rho$=1 gram/cm$^3$ $$\Delta h = \frac{((85060 - 30620) - 39130)(\text{gram/cm})(\text{cm}_2 - \text{sec}^2)}{1 \text{gram/cm}^3 * 981 \text{cm/sec}^2}$$

$\Delta h$=+15.6 cm (The patient is 15.6 cm above the membrane)

The patient head height can be established at the beginning of each fill. Any changes in the head height that occur during the fill can be attributed to an increase in intraperitoneal pressure (IPP) since the patient is asleep.

Figure 12:
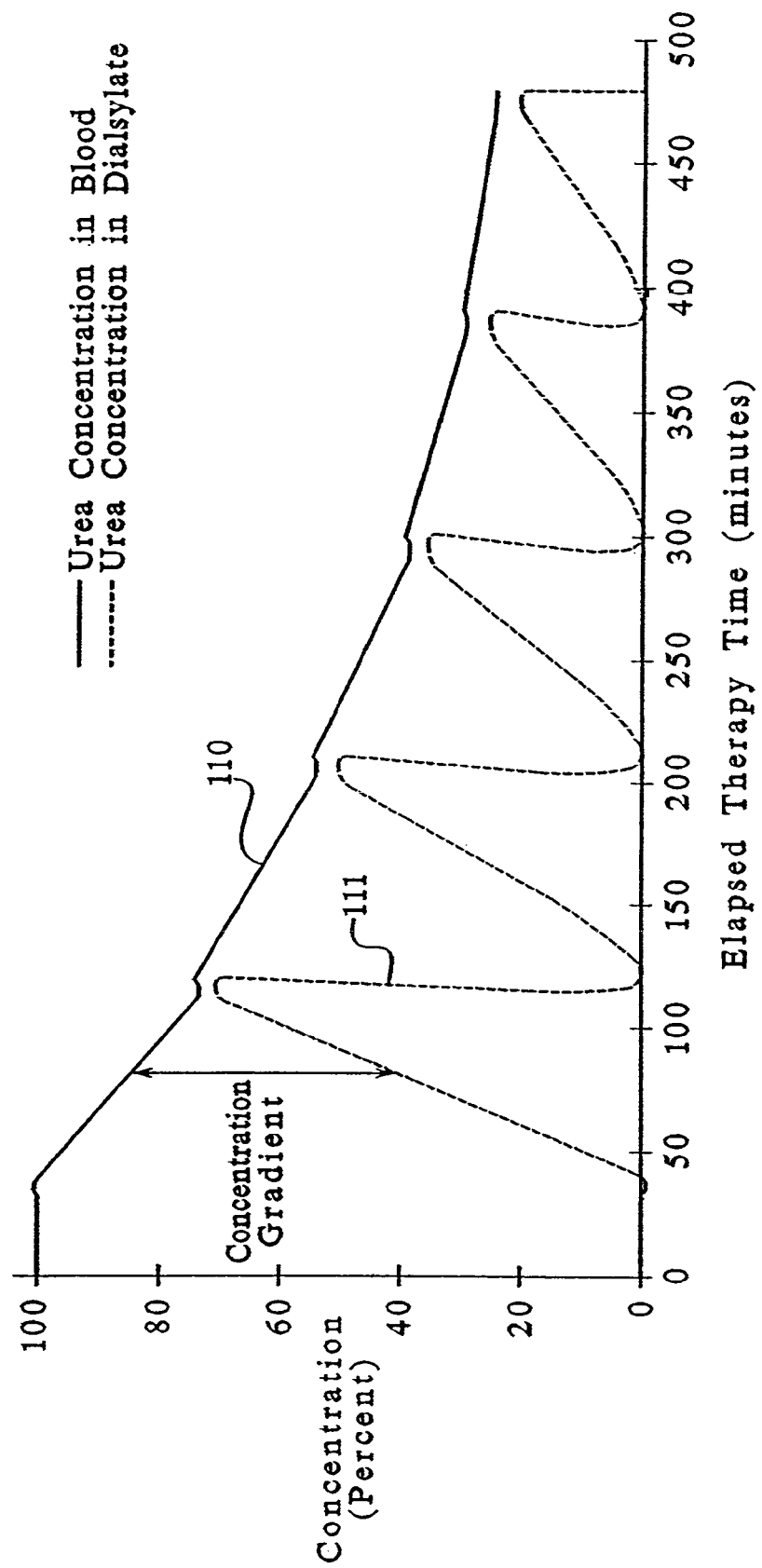
FIG. 12 illustrates, graphically, the urea concentration in blood and the urea concentration in a dialysate during a multiple dwell dialysis session.
Figure 13:
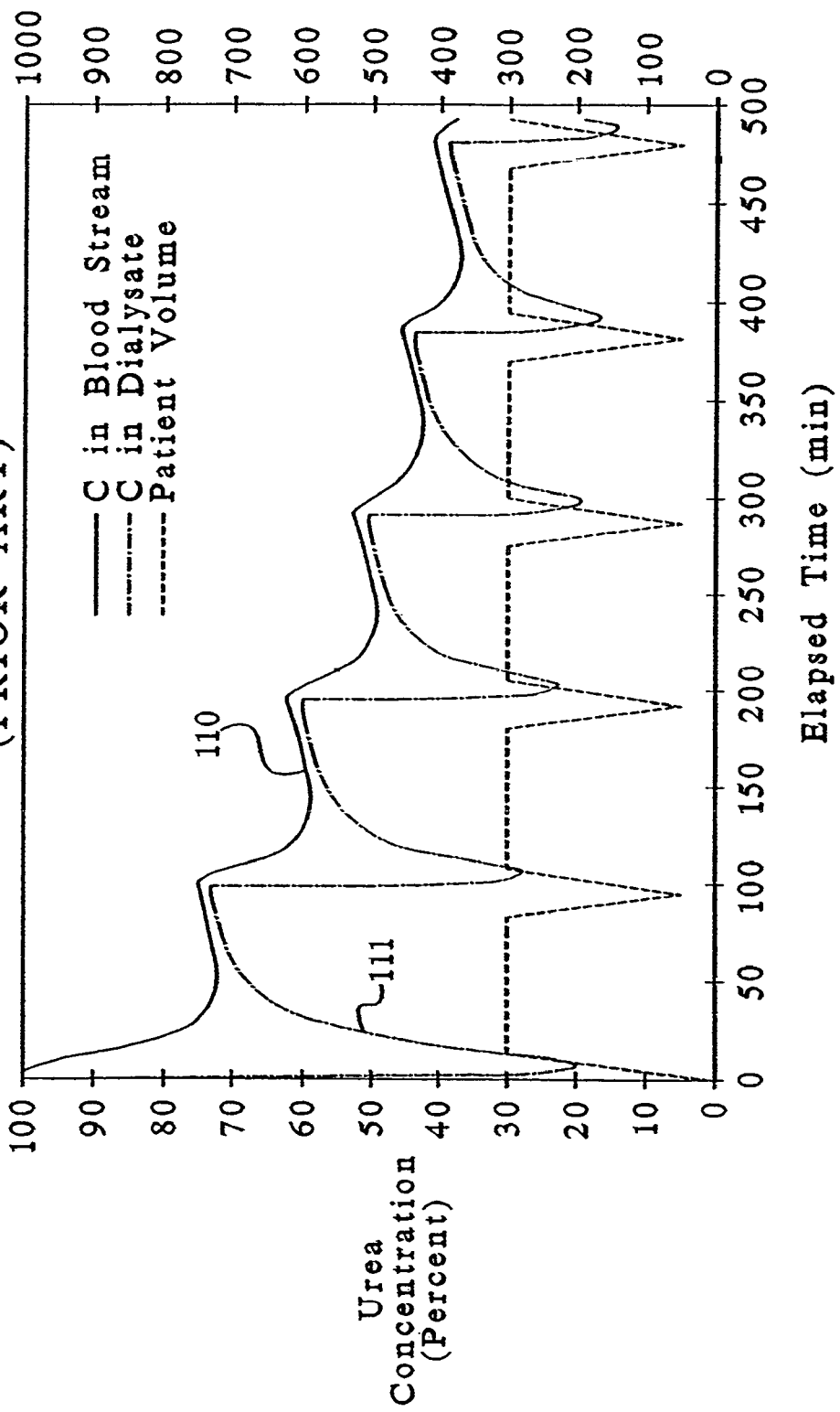
FIG. 13 illustrates, graphically, the concentration of urea in a patient's bloodstream versus the concentration of urea in a dialysate solution for an automated peritoneal dialysis solution practiced in accordance with the prior art.
Figure 14:
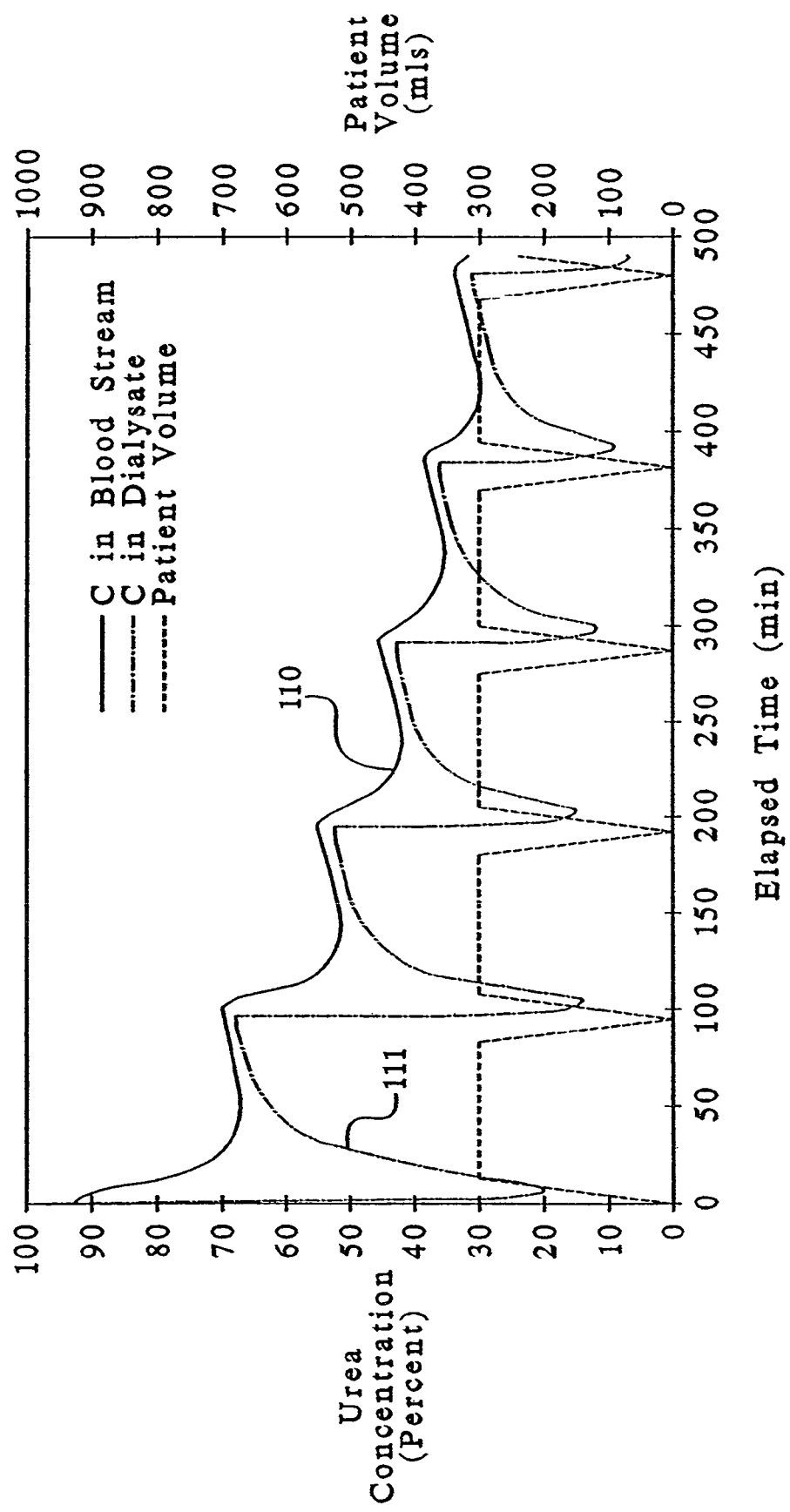
FIG. 14 illustrates, graphically, the concentration of urea in a patient's bloodstream versus the concentration of urea in a dialysate for an automated peritoneal dialysis therapy session carried out in accordance with the present invention.

Turning to FIG. 12, the concentration gradient between the urea concentration 110 in the patient's blood and the urea concentration 111 in the dialysate for typical APD cyclers is illustrated graphically. Comparing the results illustrated in FIGS. 13 and 14, it is evident that APD cyclers equipped with the sensors of the present invention provide superior results. Specifically, the data illustrated graphically in FIG. 13 was obtained using a prior art APD cycler. The data obtained in FIG. 14 was obtained using an APD cycler utilizing two sensors for monitoring intraperitoneal pressure. Note that the urea concentration 110 in the bloodstream is lower in FIG. 14 than in FIG. 13. Further note, the dialysate volume or fill volume is lower for the therapy illustrated in FIG. 14 than the therapy illustrated in FIG. 13. Thus, the present invention provides improved urea clearance with lower fill volumes.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis system comprising:
  a cycler including first and second pressure sensors, the cycler being operable with a disposable cassette including first and second sensing locations, the cassette connected to a patient line, which is capable of being placed in fluid communication with a catheter having access to a patient's peritoneal cavity, the cycler constructed and arranged to:
  convey dialysis fluid to the peritoneal cavity through the patient line and the catheter during a patient fill phase;
  allow the dialysis fluid to dwell within the peritoneal cavity during a patient dwell phase;
  convey dialysis fluid away from the peritoneal cavity through the patient line and the catheter during a patient drain phase; and
  sense, at the first and second sensing locations on the disposable cassette via the first and second pressure sensors contacting the first and second sensing locations, respectively, a pressure through the catheter to optimize an amount of fluid conveyed during the patient fill phase, so that the peritoneal cavity is not overpressurized during the patient dwell phase.

2. The peritoneal dialysis system of claim 1, the cycler further constructed and arranged to repeat the conveying, dwelling, and sensing operations at least once.

3. The peritoneal dialysis system of claim 1, the cycler including first and second pump actuators cooperating with first and second pump chambers, respectively, to (i) convey dialysis fluid to the peritoneal cavity and (ii) convey dialysis fluid away from the peritoneal cavity.

4. The peritoneal dialysis system of claim 1, wherein the cycler is constructed and arranged to sense the pressure, which includes an intraperitoneal pressure (IPP), during the fill phase.

5. The peritoneal dialysis system of claim 1, wherein the first and second pump actuators are alternating pump actuators to convey dialysis fluid substantially continuously.

6. A peritoneal dialysis system comprising:
  source of dialysis fluid;
  a disposable cassette including a sensing location;
  a first flow path from the source of dialysis fluid to the disposable cassette and from the disposable cassette to a patient;
  a second flow path from the patient to the disposable cassette and from the disposable cassette to a dialysis fluid drain;
  a cycler including a pressure sensor, the cycler being constructed and arranged to operate with the disposable cassette to:
    (i) convey dialysis fluid from the source of dialysis fluid through the first flow path to the patient and from the patient through the second flow path to the dialysis fluid drain using a pair of membrane pumps alternating to form an at least substantially continuous flow; and
    (ii) sense, at the sensing location on the disposable cassette via the pressure sensor contacting the sensing location, a pressure to optimize an amount of fluid flowing through at least one of the first flow path and the second flow path.

7. The peritoneal dialysis system of claim 6, the cycler including two sensors for sensing the pressure, which includes an intraperitoneal pressure, to perform the at least one optimization.

8. The peritoneal dialysis system of claim 7, the two sensors sensing pressure at the disposable cassette.

9. The peritoneal dialysis system of claim 6, the cycler constructed and arranged to reverse a direction of flow in at least one of the first and second flow paths.

10. The peritoneal dialysis system of claim 6, the cycler further constructed and arranged to sense the pressure while conveying the dialysis fluid.

11. The peritoneal dialysis system of claim 6, the cassette including a plurality of pressure sensing locations.

12. A peritoneal dialysis system comprising:
   a disposable cassette including first and second sensing locations; and
   a cycler including first and second pressure sensors, the cycler being constructed and arranged to:
   (i) a convey dialysis fluid from a dialysis fluid container through a catheter to a patient;
   (ii) allow the dialysis fluid to dwell within the patient;
   (iii) reverse a direction of dialysis fluid flow in the catheter away from the patient; and
   (iv) sense, at the first and second sensing locations on the disposable cassette using the first and second pressure sensors provided by the cycler and placed in contact with the first and second sensing locations, respectively, the sensing locations in fluid communication with the catheter, a pressure to optimize at least one of an amount of fluid flowing towards or away from the patient, so that the patient is comfortable while the dialysis fluid dwells within the patient.

13. The peritoneal dialysis of claim 12, the cycler operating a fluid control valve to reverse the direction of dialysis fluid.

14. The peritoneal dialysis system of claim 12, the disposable cassette including a flexible membrane, the two sensors placed in contact with the membrane at the first and second sensing locations for sensing the pressure to perform the at least one optimization.

15. The peritoneal dialysis system of claim 12, the cycler constructed and arranged to flow fluid away from the patient by pumping fluid towards a disposable cassette operating with the cycler.

16. The peritoneal dialysis system of claim 12, the cycler constructed and arranged to repeat the conveying, dwelling, reversing and sensing operations at least once.

17. The peritoneal dialysis system of claim 12, the cycler constructed and arranged to perform the sensing operation during the conveying or reversing operations.

18. The peritoneal dialysis system of claim 12, the cycler including a pair of medical fluid pumps alternating to pump dialysis fluid substantially continuously for the conveying and reversing operations.

19. A peritoneal dialysis system comprising:
   a disposable cassette including a sensing location; and
   a cycler including a pressure sensor, the cycler being constructed and arranged to:
   (i) pump substantially continuously using a pair of alternating pumps to convey dialysis fluid to a peritoneal cavity through a catheter during a patient fill phase;
   (ii) allow the dialysis fluid to dwell within the peritoneal cavity during a patient dwell phase;
   (iii) pump substantially continuously using the pair of alternating pumps to convey dialysis fluid away from the peritoneal cavity through the catheter during a patient drain phase; and
   (iv) measure, at the sensing location on the disposable cassette via the pressure sensor contacting the sensing location, a pressure through the catheter to optimize an amount of fluid conveyed during the patient fill phase, so that the peritoneal cavity is not overpressurized during the patient dwell phase.

20. The peritoneal dialysis system of claim 19, the cycler including two pressure sensors, each pressure sensor operable with a respective sensing location of a disposable cassette to measure the pressure.

21. A peritoneal dialysis system comprising:
   a cycler;
   a disposable cassette operable with the cycler;
   a patient line extending from the disposable cassette, the patient line connectable to a catheter having access to a patient's peritoneal cavity;
   first and second pressure sensors provided by the cycler;
   corresponding first and second sensing locations on the disposable cassette located, in operation, directly adjacent to and contacting the first and second pressure sensors;
   a patient fill phase performed by the cycler;
   a patient dwell phase performed by the cycler;
   a patient drain phase performed by the cycler; and
   wherein the patient fill phase is controlled by the cycler and at lease one of the pressure sensors, so that the peritoneal cavity is not overpressurized during the dwell phase.

22. The peritoneal dialysis system of claim 21, wherein the cycler is configured to sense the intraperitoneal pressure during the fill phase.

23. A peritoneal dialysis system comprising:
   a cycler;
   a disposable cassette operable with the cycler;
   a patient line extending from the disposable cassette, the patient line connectable to a catheter having access to a patient's peritoneal cavity;
   first and second pressure sensors provided by the cycler;
   corresponding first and second sensing locations on the disposable cassette that are in contact with first and second pressure sensors of the cycler and are separate from pumping locations and valving locations of the disposable cassette;
   a patient fill phase performed by the cycler;
   a patient dwell phase performed by the cycler;
   a patient drain phase performed by the cycler; and
   wherein the patient drain phase is controlled by the cycler and one of the pressure sensors so as not to apply too much negative pressure during the patient drain phase.

24. The peritoneal dialysis system of claim 23, wherein the pressure sensor used during the drain phase is a vacuum pressure sensor, the other pressure sensor a positive pressure sensor.

* * * * *